United States Patent [19]

Gast

[11] Patent Number: 5,495,363
[45] Date of Patent: Feb. 27, 1996

[54] MIRROR OPTICS WITH GRAZING INCIDENCE REFLECTION

[75] Inventor: Jürgen Gast, Rheinstetten, Germany

[73] Assignee: Bruker Analytische Messtechnik Gmbh, Rheinstetten, Germany

[21] Appl. No.: 167,482

[22] Filed: Dec. 15, 1993

[30] Foreign Application Priority Data

Dec. 19, 1992 [DE] Germany .............. 42 43 146.8

[51] Int. Cl.⁶ ............................................. G02B 17/00
[52] U.S. Cl. ............... 359/351; 359/352; 359/356; 359/357; 359/366; 359/731; 359/857; 359/859; 359/861; 250/339.08
[58] Field of Search ............... 359/351, 352, 359/356, 357, 366, 730, 731, 387, 864, 859, 370, 371, 861, 857, 850, 858, 726, 727, 729; 250/339.08, 339.12; 378/84, 85

[56] References Cited

U.S. PATENT DOCUMENTS

| | | | |
|---|---|---|---|
| 2,306,679 | 12/1942 | Warmisham | 359/859 |
| 3,827,778 | 8/1974 | Wheeler | 359/365 |
| 3,927,254 | 12/1975 | Lessman | 359/356 |
| 4,015,120 | 3/1977 | Cole | 250/216 |
| 4,521,068 | 6/1985 | Schulte in den Bäumen | 250/353 |
| 4,712,912 | 12/1987 | Messerschmidt | 356/445 |
| 4,810,077 | 3/1989 | Sting | 359/387 |
| 5,051,602 | 9/1991 | Sting et al. | 356/445 |
| 5,144,496 | 9/1992 | Kashima | 359/859 |
| 5,291,340 | 3/1994 | Kashima | 359/859 |

FOREIGN PATENT DOCUMENTS

| | | | |
|---|---|---|---|
| 0116321 | 8/1984 | European Pat. Off. | G02B 21/00 |
| 3303140 | 8/1984 | Germany | G01J 3/28 |
| 3704239 | 8/1987 | Germany | G02B 21/10 |

*Primary Examiner*—Paul M. Dzierzynski
*Assistant Examiner*—John Juba, Jr.

[57] ABSTRACT

In an infrared (IR) microscope for a Fourier transform (FT) infrared spectrometer with a Cassegrain mirror-lens with which an incident beam (15) can be focused via a convex mirror (16) and a concave mirror (17) onto a first point-shaped region (19) on the surface of a sample (20) under an angle of incidence β<60° relative to the optical axis (22) and subsequent to travelling through an optical path x, a first planar mirror (1) and a second planar mirror (2) are arranged between the concave mirror (17) and the surface of the sample (20) such that the luminous beam (30) reflected from the concave mirror (17) in the direction of the sample (20) is focused onto the first planar mirror (1), onto the second planar mirror (2), then onto a second point-shaped region (19') on the surface of the sample (20), the second point-shaped region lying on the optical axis (22) closer to the lens (16, 17) than the first point-shaped region (19), whereby the sum of the optical paths is equal to the optical path x, whereby the angle of incidence β' is larger than 60° and whereby a third planar mirror (3) and a fourth planar mirror (4) are arranged symmetrically with respect to the second (2) and first (1) planar mirrors.

7 Claims, 3 Drawing Sheets

MIRROR OPTICS WITH GRAZING INCIDENCE REFLECTION

BACKGROUND OF THE INVENTION

The invention concerns an infrared (IR) microscope for a Fourier transform (FT)-IR spectrometer having a Cassegrain mirror-lens, with which an incident infrared luminous beam can be focused by means of a convex mirror configured rotationally symmetric with respect to the optical axis of the Cassegrain mirror-lens and by means of a concave mirror which is likewise rotationally symmetric to the optical axis of the lens under an angle of incidence $\beta<60°$ with respect to the optical axis of the lens after travelling along an optical path x onto a first point-shaped region on the surface of a sample, the region being simultaneously the hypothetical point of intersection of the optical axis of the lens through the sample surface.

An IR microscope of this type is, for example, known in the art from publication DE-OS 33 03 140.

The known IR microscope is utilized in an FTIR spectrometer for the analyses of gaseous, liquid and, preferentially, solid samples of macroscopic size. Thereby it is also possible to measure microscopic regions of the sample surface in a point-like fashion, whereby the measurements are carried out in reflection.

A disadvantage of the known IR microscope is that the IR luminous beam which is focused onto the sample surface is incident upon this surface at an incidence angle $\beta<60°$ with respect to the optical axis of the lens. In special applications, in particular when the interaction of the incident IR radiation with the sample surface must be intensified, a substantially larger angle of incidence $\beta'$ can be desirable in order to increase the usable measuring signals which, in an extreme case, would be in the vicinity of 90° so that the incident IR luminous beam nearly grazes the sample surface.

Although there are special-grazing-angle microscopes such as for example, that known from the arrangement of publication DE-OS 37 04 239, these known apparatuses utilize lenses which are highly specialized and expensive and are adapted solely for the case of grazing incidence of the luminous beam onto the sample surface.

It is therefore the purpose of the present invention to present an IR microscope, which in large part corresponds to that described above, and distinguishes itself therefrom solely through a small number of simple and inexpensive optical components with which it can be reconfigured from the original steeper angle of incidence to a nearly grazing incidence of the IR luminous beam onto the sample surface, whereby the imaging properties should be maintained, the optical path lengths which the radiation travels in the IR microscope up to the sample should remain constant and whereby, subsequent to the reconfiguration, the infrared luminous beam incident on the sample surface should still remain focused.

SUMMARY OF THE INVENTION

This purpose is achieved in accordance with the invention in that between the concave mirror and the surface of the sample, a first planar mirror and a second planar mirror are so arranged that the luminous beam reflected from the concave mirror in the direction of the sample is focused, following an optical path $x_1$, onto the first planar mirror and, after an optical path $x_2$ onto the second planar mirror and, after an optical path $x_3$ onto a second point-shaped region on the surface of the sample, the region likewise lying on the optical axis of the lens but closer to the lens than the first point-shaped region, whereby the sum of the optical paths $x_1+x_2+x_3$ is equal to the optical path x, and whereby the angle of incidence $\beta'$ between the luminous beam incident on the sample surface and the optical axis of the lens is larger than 60° and whereby a third planar mirror and a fourth planar mirror are provided for which are arranged symmetrically, relative to the optical axis, to the first and the second planar mirror respectively in order to guide the light reflected from the second point-shaped region back through the IR microscope.

With the solution in accordance with the invention the primary parts of the IR microscope, in particular, the Cassegrain mirror-lens continue to be utilized, whereby a reconfiguration from a steep angle of incidence $\beta$ to a flat angle of incidence $\beta'$ can transpire by means of a simple insertion or positioning-in of the four planar mirrors in the appropriate geometric configuration. In the operation mode having a flat angle of incidence $\beta'$ or grazing incidence of the IR radiation onto the sample surface, it is necessary to arrange the sample geometrically closer to the lens so that the optical paths remain constant with respect to the mode of operation having the steeper angle of incidence $\beta$ so that a focusing of the radiation incident on the sample is guaranteed.

A further advantage of the configuration in accordance with the invention is that, in the mode of operation having the flat angle of incidence $\beta'$ in which the sample is displaced in the direction of the lens, the planar mirrors utilized are self-collimating so that no additional collimators are needed in the configuration.

In an embodiment of the inventive IR microscope, the angle of incidence $\beta'$ between the luminous beam incident on the surface of the sample and the optical axis of the Cassegrain mirror-lens assumes a value between 75° and 85°. Such a flat angle of incidence, which comes very close to the case of grazing incidence radiation is just barely possible technically, whereby a substantially sized measurement spot is already produced on the sample surface by the incident luminous beam.

In a preferred embodiment the first and fourth planar mirrors are integral with another and constructed from a two-sided mirrored body. In this fashion components are saved in the inventive IR microscope, the mounting of the reconfiguration components for the steep to the flat angle of incidence is simplified, and a subsequent alignment of the infrared microscope becomes easier.

In a particularly preferred embodiment all planar mirrors are arranged on a common frame which is fastened to the Cassegrain mirror-lens in a detachable fashion. In this manner only one single component, namely the frame with the mounted planar mirrors, is necessary for reconfiguration of the IR microscope from a steep to a flat angle of incidence.

In a further particularly preferred embodiment of the inventive IR microscope the first and the fourth planar mirrors are arranged parallel to the optical axis of the Cassegrain mirror-lens. In this fashion the mounting of the components for reconfiguration from steep to flat angle of incidence is even easier.

In a likewise preferred embodiment the luminous beam is linearly polarized, whereby the direction of polarization can be parallel or perpendicular to the plane of incidence of the luminous beam onto the surface of the sample. With grazing incidence this has the advantage with certain samples (namely thin layers on metal) of a substantially higher sensitivity of the spectrometer to the measuring substance since the E-vector of the electromagnetic radiation incident on the sample is polarized in the plane of incidence.

In another preferred embodiment of the invention the infrared microscope further comprises an attenuated total reflection (ATR) crystal having a surface in contact with surface of the sample. This embodiment has the advantage that even samples with poor surface reflection characteristics can be examined in the microscope with the assistance of the ATR crystal.

The invention also includes a Cassegrain mirror-lens with four planar mirrors for use in an IR microscope of the inventive kind described above.

An insert with mounted planar mirrors for installation in this type of Cassegrain mirror-lens is also within the framework of the invention.

The invention is described more closely and explained below with reference to the embodiments represented in the drawing. The features which can be derived from the description and the drawing can be used in other embodiments of the invention either individually or collectively in arbitrary combination.

DESCRIPTION OF THE PREFERRED EMBODIMENT

Figure 1:
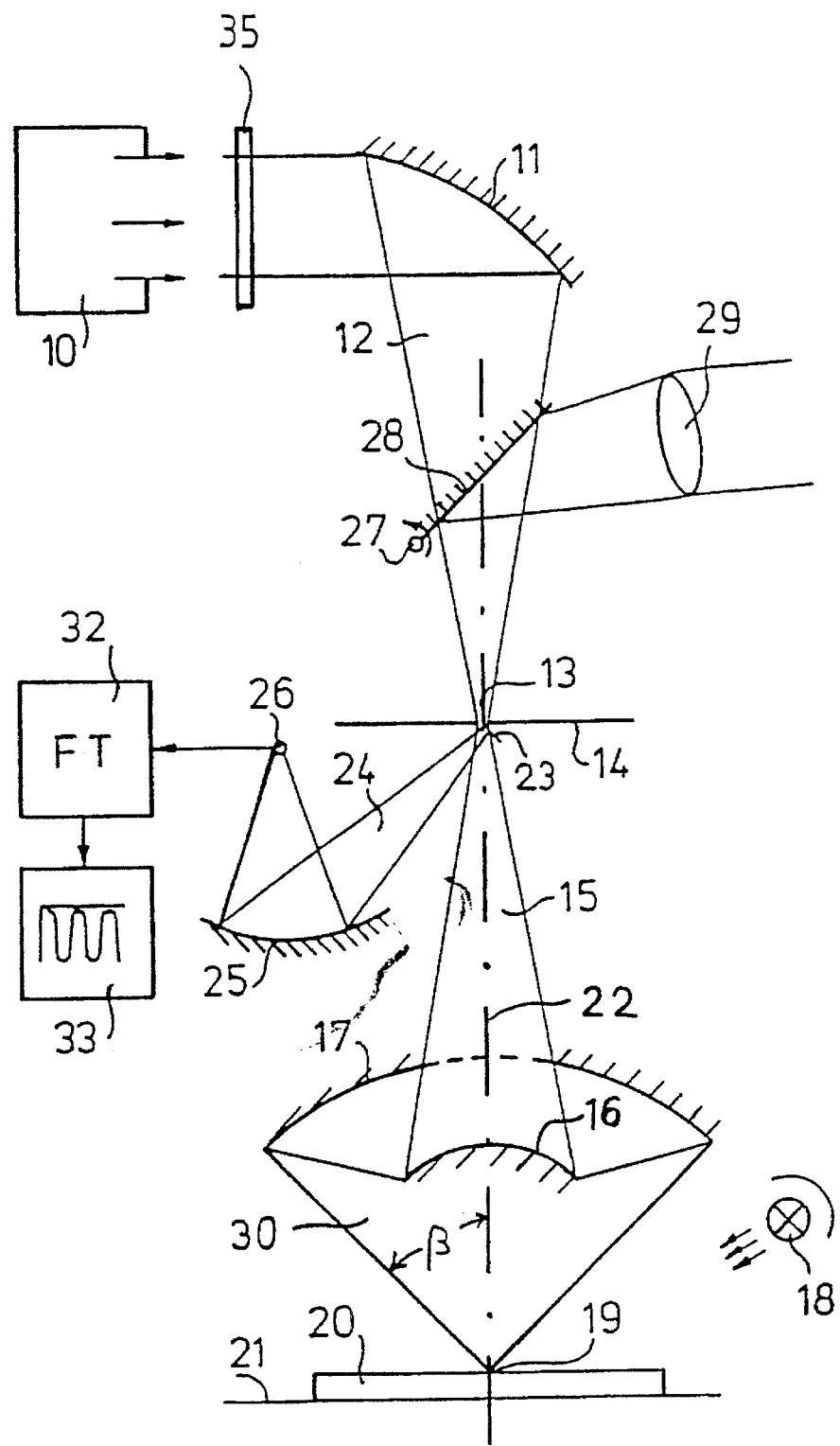
FIG. 1 shows a functional diagram with a schematic optical path through an FTIR spectrometer with a Cassegrain mirror-lens.

In the optical path of an FTIR spectrometer according to prior art shown in FIG. 1, an infrared light source 10 radiates a largely parallel light beam. This parallel light beam impinges on a collimator mirror 11 and is deflected therefrom into a converging luminous beam 12.

The luminous beam 12 is focused onto a collimator opening 13 in a plate 14. The collimator opening 13 is, in the simplest case, simply an opening in the plate 14. It is, however, also possible to have a varied collimator opening 13. This can, on the one hand, be effected by a set of fixed collimators of varying opening sizes which are exchanged with another. Alternatively, continuously adjustable collimators can also be used, for example, of the kind having circular-shaped cross sections and radially moving segments or with rectangular-shaped cross sections formed by arranging two slot collimators in tandem at right angles.

After passing through the collimator opening 13 the luminous beam 15 which at this point is divergent is incident on mirror-lens 16, 17, with an optical axis 22, the mirror-lens focusing the incident divergent luminous beam 15 onto a point-shaped region 19 of a sample 20 arranged on a base 21.

The sample can, thereby, also be illuminated by a light source 18 which radiates in the visible region, whereby the light source 18 can, preferentially, be switched off during the measurement.

The light directly reflected by the sample 20 travels, due to the perpendicular configuration with respect to the sample surface of the axis of the luminous beam focused onto the sample 20, back through the same path described above and is thereby incident on a, preferentially pivotable, deflecting mirror 23 which is arranged directly in front of the collimator opening 13. The deflecting mirror 23 covers, by way of example, 50% of the collimator opening 13 and reflects light incident upon it from mirror-lens 16, 17 into a divergent luminous beam 24, which is focused via a collimating mirror 25 onto a detector 26.

This detector 26 then converts the measurement light incident upon it into a corresponding electrical signal and directs this to a computer 32 which, preferentially, functions with the assistance of a Fourier transformation (FT). In addition, a display 33 upon which the measured infrared spectrum can be observed, written out, or in some other fashion documented, is also connected to the computer 32. By way of example, the display 33 can be a screen or a plotter.

Finally, another deflecting mirror 28, which is preferentially pivotable about an axis 27, is provided in the region between the collimator opening 13 and the collimator mirror 11 to deflect the luminous beam incident upon it from the mirror-lens 16, 17 and introduce it to an observation unit for visual observation as indicated by the lens 29.

As one can easily see from the optical path of FIG. 1, the aperture 13 is imaged onto the sample 20 with the magnification of the mirror-lens 16, 17. In a typical embodiment the mirror lens 16, 17 has a magnification of 15, so that a collimator opening of 1 mm diameter leads to a point-shaped region 19 which has a diameter of only 70 µm. The imaging of the collimator opening 13 thereby leads to extremely small point-shaped regions 19 and thereby to a high spatial resolution of the point-shaped measurement on the sample 20.

The collimator opening 13 thereby initially defines, by means of the described imaging, the point-shaped region 19 on the sample 20 and also likewise defines via the lens 29 the visual observation region so that the measuring region and the observation region are fundamentally identical in the described configuration.

Figure 2B:
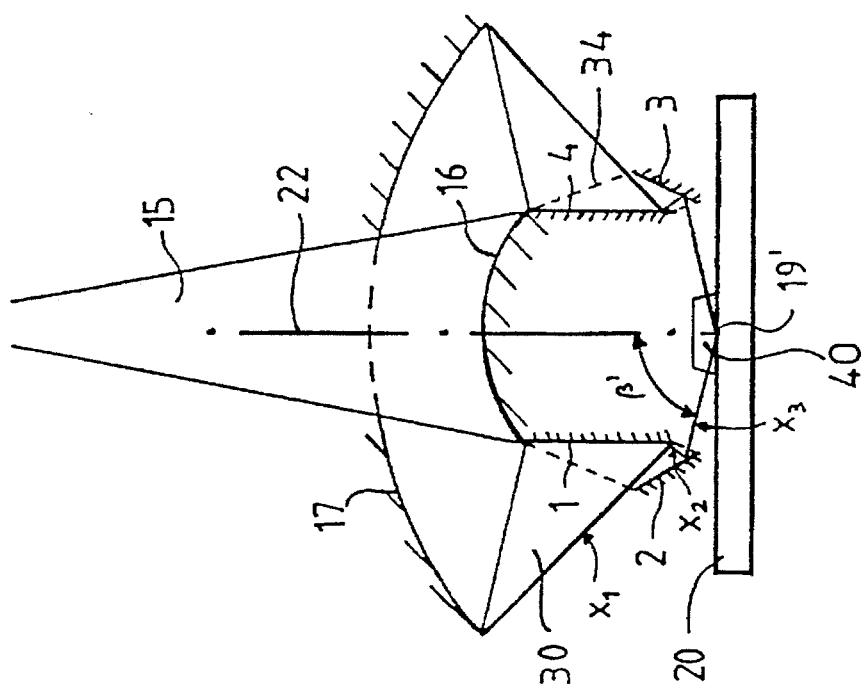
FIG. 2b shows the schematic optical path as in FIG. 2a, but modified in accordance with the invention with four planar mirrors in order to achieve a nearly grazing radiation incidence on the sample surface.
Figure 2A:
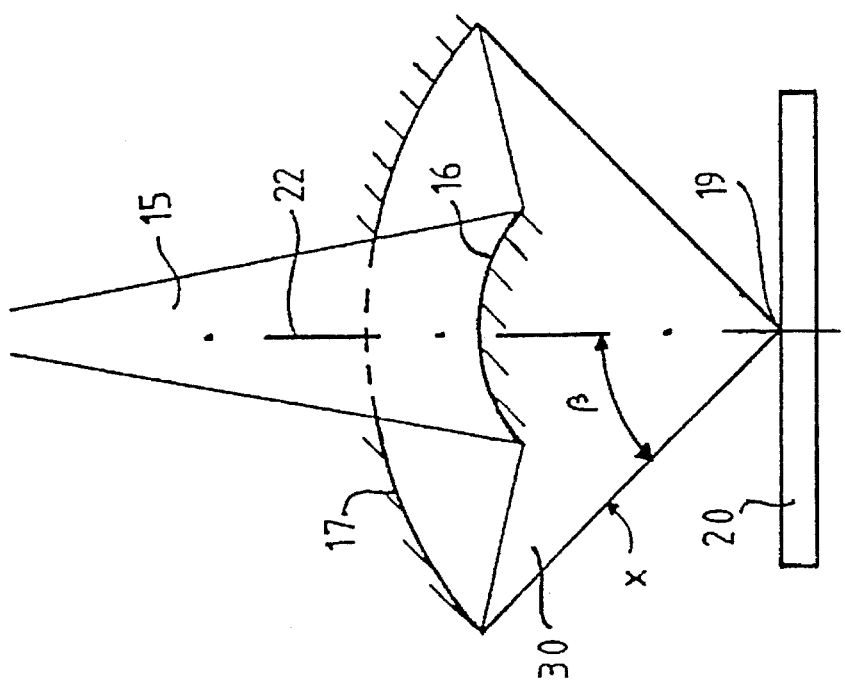
FIG. 2a shows the schematic optical path through a conventional Cassegrain mirror-lens.

FIG. 2a shows the optical path through a conventional Cassegrain mirror-lens with a convex mirror 16, which is rotationally symmetric with respect to the optical axis 22, by means of which the initially divergent luminous beam 15 is deflected onto the concave mirror 17 which is likewise rotationally symmetric with respect to the optical axis 22 and therefrom focused as luminous beam 30 onto the point-shaped region 19 of the sample 20. The angle of incidence β of the focused IR radiation luminous beam 30 incident on the sample surface is relatively steep with respect to the optical axis 22, but in any event smaller than 60°. The IR radiation of the luminous beam 30 reflected from the concave mirror 17 thereby travels through an optical path x between the concave mirror 17 and the surface of the sample 20.

In the inventively modified Cassegrain mirror-lens shown in FIG. 2b, the luminous beam 30 reflected from the concave mirror 17 is initially deflected via an optical path $x_1$ onto a first planar mirror 1 and from there is reflected via second optical path $x_2$ onto a second planar mirror 2 wherefrom it then, via an optical path $x_3$, is focused onto a small focal spot 19' on the surface of the sample 20. The angle of incidence β' of the infrared radiation incident on the surface of the sample which is thereby achieved is substantially larger than 60° relative to the optical axis 22, and, in an advantageous case, can nearly graze the sample surface.

In order to maintain the focusing properties of the Cassegrain mirror-lens without changing the concave mirror 16, 17, the sum of the optical paths $x_1+x_2+x_3=x$. The focal spot 19' is thereby closer by a distance d to the Cassegrain mirror-lens than the point-shaped region 19 upon which the infrared radiation incident on the lens, without the modifying inventive four planar mirrors 1 through 4, is focused. Since the focal spot 19' is closer to the lens, the configuration, in addition, is self-collimating.

The entire configuration is symmetric to the optical axis 22 so that the luminous beam focused on the surface of the sample 20, after reflection from the sample surface, is deflected onto a third planar mirror 3 configured symmetrically with respect to the second planar mirror 2 and from there onto a fourth planar mirror 4 which is arranged symmetrically to the first planar mirror, wherefrom it is guided to a concave mirror 17, to a convex mirror 16 and finally to the collimator opening 13.

FIG. 2b also indicates the possible incorporation of an attenuated total reflection (ATR) crystal. ATR crystals can be used in applications involving samples with very poor surface reflection characteristics. The crystal surface in contact with the sample totally internally reflects the incident beam with a small fraction of the electric field vector in the beam penetrating through the surface into the sample so that optical sampling of the sample is achieved. Advantageously the surfaces of the crystal into which the beam enters and through which the beam exits are adapted to be perpendicular to the optical path of the beam so that no displacement of the beam is effected through the insertion of the crystal.

Figure 3:
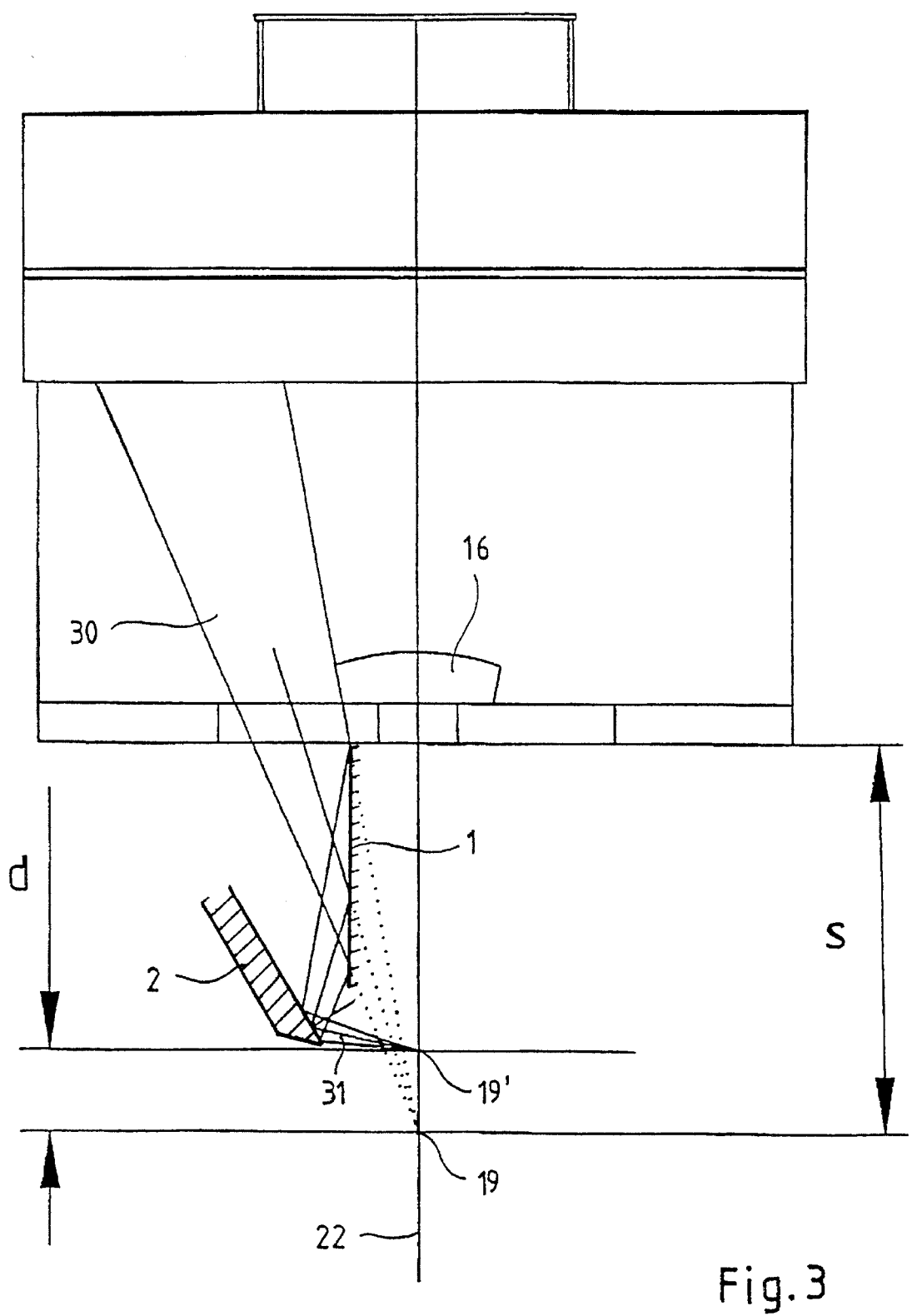
FIG. 3 shows one half side of an enlarged schematic representation of the optical path through a modified Cassegrain mirror-lens in accordance with the invention compared to a conventional one.

FIG. 3 shows the optical path of an infrared luminous beam 30 incident on the sample after deflection by the first planar mirror 1 and the second planar mirror 2 and is illustrated as a nearly grazingly incident luminous beam 31 (solid line) compared to the luminous beam 30 (dotted line) focused onto a point-shaped region 19 without benefit of the modification of the first planar mirror 1 and the second planar mirror 2. The separation d in the direction of the optical axis 22 between the point-shaped region 19 and the focal spot 19' assumes, in an embodiment of the inventive configuration, a value of 5.13 mm when the separation s from the lower edge of the Cassegrain mirror-lens 16, 17 up to the sample surface in the conventional unmodified case is 24.00 mm.

It is possible, without excessive technical effort, to use the inventive modification to produce an angle of incidence β' between the luminous beam 31 incident on the sample surface and the optical axis 22 of the Cassegrain mirror-lens 16, 17, in the region between 75° and 85°, whereby the focal spot 19' on the sample surface is already substantially increased.

It is preferred that the first and the fourth planar mirrors 1, 4 are produced from one integral body mirrored on both sides; this however, is not visible in the cross-sectional view of FIG. 2b and FIG. 3.

In the embodiment shown in FIG. 2b all planar mirrors 1 through 4 are arranged on a common frame 34 which is fastened in a detachable fashion to the Cassegrain mirror-lens 16, 17. The frame 34 is indicated by the dashed lines.

A particularly simple mounting of the planar mirror is achieved if the first and the fourth planar mirrors 1, 4 are arranged parallel to the optical axis 22 of the Cassegrain mirror-lens 16, 17.

With the nearly grazing incidence of the infrared radiation onto the sample surface in the inventive modification it is possible to achieve a particularly high sensitivity to the measuring substance in that the luminous beam 31 is linearly polarized with the assistance of a polarizer 35 whereby the polarization direction runs parallel to the plane of incidence of the luminous beam 31 on the surface of the sample 20.

We claim:

1. In an improved infrared (IR) microscope for a Fourier transform (FT) IR spectrometer comprising a Cassegrain mirror-lens having an optical axis, the lens comprising a convex mirror and a concave mirror which are both rotationally symmetric to the optical axis, the lens being arranged for focusing, at an angle of incidence β<60° relative to the axis of the lens and after travelling through an optical path length x from the concave lens, an incident IR beam onto a first point-shaped region on the surface of a sample, the point-shaped region simultaneously constituting the point of intersection of the optical axis of the lens through a sample surface, the improvement comprising a first planar mirror and a second planar mirror arranged between the concave mirror and the surface of the sample wherein the beam reflected from the concave mirror in the direction of the sample is focused, following an optical path length $x_1$, onto the first planar mirror and, following an optical path length $x_2$, impinges on the second planar mirror, and after an optical path length $x_3$, is incident on a second point-shaped region on the surface of a sample, the second pointed-shaped region also lying on the axis of the lens but closer to the lens than the first point-shaped region, whereby the sum of the optical path lengths $x_1+x_2+x_3$ is equal to the optical path length x, and an angle of incidence β' between the beam incident on the sample surface and the axis of the lens is larger than 60° and further comprising a third and a fourth planar mirror arranged, relative to the optical axis, symmetrically with respect to the second and first planar mirrors respectively, the third and fourth mirrors being arranged for guiding the light reflected from the second point-shaped region back through the IR microscope.

2. The IR microscope of claim 1, wherein the angle of incidence β' between the beam incident on the surface of the sample and the optical axis of the Cassegrain mirror-lens assumes a value between 75° and 85°.

3. The IR microscope of claim 1, wherein the first and the fourth planar mirrors are built from a single body, mirrored on both sides.

4. The IR microscope of claim 1, wherein the first and the fourth planar mirrors are arranged parallel to the optical axis of the lens.

5. The IR microscope of claim 1, wherein polarizing means are provided for linearly polarizing the beam in a direction of polarization which is parallel to a plane of incidence of the beam onto the surface of the sample.

6. The IR microscope of claim 1, further comprising an attenuated total reflection (ATR) crystal having a surface in contact with the surface of the sample.

7. An improved Cassegrain mirror-lens having an optical axis, and a convex mirror and a concave mirror which are both rotationally symmetric to the optical axis, the lens being arranged for focusing, at an angle β<60° relative to the optical axis of the lens and after travelling through an optical path length x from the concave lens, an incident beam onto a first point-shaped region in a focal plane along the optical axis of the lens, the improvement comprising:

a first planar mirror and a second planar mirror arranged between the concave mirror and said focal plane such that a beam reflected from the concave mirror in the direction of said focal plane is focused, following an optical path length $x_1$, onto the first planar mirror and, following an optical path length $x_2$, impinges on the second planar mirror, and after an optical path length $x_3$, is incident on a second point-shaped region on said focal plane, the second point-shaped region also lying on the axis of the lens but closer to the lens than the first point-shaped region, whereby the sum of the optical path lengths $x_1+x_2+x_3$ is equal to the optical path length x, and an angle of incidence $\beta'$ between the beam incident on said focal plane and the axis of the lens is larger than 60°, and further comprising a third and a fourth planar mirror arranged, relative to the optical axis, symmetrically with respect to the second and first planar mirrors respectively, the third and fourth mirrors being arranged for guiding the light reflected from the second point-shaped region.

* * * * *